(12) United States Patent
Gore et al.

(10) Patent No.: US 8,946,265 B2
(45) Date of Patent: Feb. 3, 2015

(54) PROCESS FOR THE PREPARATION OF LENALIDOMIDE

(75) Inventors: Vinayak Govind Gore, Maharashtra (IN); Vinay Kumar Shukla, Maharashtra (IN); Shreyas Shrikant Bhandari, Maharashtra (IN); Suresh Hasbe, Maharashtra (IN)

(73) Assignee: Generics [UK] Limited, Hertfordshire (GB)

(*) Notice: Subject to any disclaimer, the term of this patent is extended or adjusted under 35 U.S.C. 154(b) by 142 days.

(21) Appl. No.: 13/254,249

(22) PCT Filed: Mar. 1, 2010

(86) PCT No.: PCT/GB2010/050352
§ 371 (c)(1),
(2), (4) Date: Dec. 6, 2011

(87) PCT Pub. No.: WO2010/100476
PCT Pub. Date: Sep. 10, 2010

(65) Prior Publication Data
US 2012/0071509 A1    Mar. 22, 2012

(30) Foreign Application Priority Data

Mar. 2, 2009   (IN) .............................. 383/KOL/2009
Mar. 16, 2009  (IN) .............................. 463/KOL/2009

(51) Int. Cl.
*C07D 211/88*   (2006.01)
*C07D 209/44*   (2006.01)
(Continued)

(52) U.S. Cl.
CPC .................................... C07D 401/04 (2013.01)
USPC ............ 514/339; 514/323; 546/201; 546/196

(58) Field of Classification Search
USPC .......................................... 546/201; 514/339
See application file for complete search history.

(56) References Cited

U.S. PATENT DOCUMENTS

| 5,635,517 A | 6/1997 | Muller et al. |
| 6,281,230 B1 | 8/2001 | Muller et al. |

(Continued)

FOREIGN PATENT DOCUMENTS

| CA | 2579291 | 3/2006 |
| IN | 47C HE2 006 | 11/2007 |

(Continued)

OTHER PUBLICATIONS

Muller (Bioorganic & Medicinal Chemistry Letters,1999, 9, 1625-1630.*

(Continued)

*Primary Examiner* — John Mabry
*Assistant Examiner* — Daniel Carcanague
(74) *Attorney, Agent, or Firm* — Fulbright & Jaworski LLP; Scott D. Rothenberger

(57) ABSTRACT

The present invention relates to improved processes for preparing 3-(4-amino-1-oxo-1,3-dihydro-isoindol-2-yl)-piperidine-2,6-dione (I) (lenalidomide) and its intermediate 3-(1-oxo-4-nitro-1,3-dihydro-isoindol-2-yl)-piperidine-2,6-dione. The present invention further relates to improved processes for preparing lenalidomide crystalline form A, use of said crystalline form A as an active pharmaceutical ingredient or as an intermediate in the preparation of further crystalline or amorphous forms of lenalidomide, compositions comprising lenalidomide crystalline form A and their use in the treatment of disease.

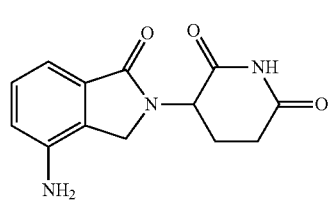

(I)

9 Claims, 4 Drawing Sheets

(51) Int. Cl.
*C07D 401/04* (2006.01)
*A61K 31/454* (2006.01)

(56) References Cited

U.S. PATENT DOCUMENTS

| | | |
|---|---|---|
| 6,335,349 B1 | 1/2002 | Muller et al. |
| 7,465,800 B2 | 12/2008 | Jaworsky et al. |
| 2005/0096351 A1 | 5/2005 | Jaworsky et al. |

FOREIGN PATENT DOCUMENTS

| | | |
|---|---|---|
| WO | WO 2005/023192 | 3/2005 |
| WO | WO 2006/028964 | 3/2006 |
| WO | WO 2008/128225 | 10/2008 |
| WO | WO 2009/077784 | 6/2009 |
| WO | WO 2009/114601 | 9/2009 |
| WO | WO 2010/061209 | 6/2010 |
| WO | WO 2011/064574 | 6/2011 |

OTHER PUBLICATIONS

Loewenthal; A Guide for the Perplexed Organic Experimentalist, Second Edition, 1990, John Wiley & Sons, Chapter 6: "Solvents".*
Anderson; Practical Process Research and Development, 2000, Academic Press, Chapter 4: "Solvent Selection".*
Nishimura; Handbook of Heterogeneous Catalytic Hydrogenation for Organic Synthesis, 2001 John Wiley & Sons, Chapter 9, "Hydrogenation of Nitro, Nitroso, and Related Compounds".*
International Search Report PCT/GB2010/050352 dated Apr. 21, 2011 (5 pgs.).
N. Jonsson, Acta Pharm. Suecica, vol. 9, pp. 524-542, 1972.
P. DiMartino et al., J. Thermal Analysis, vol. 48, pp. 447-458, 1997.
K. Knapman, Modern Drug Discovery, pp. 53-57, 2000.
Caira, "Crystalline Polymorphism of Organic Compounds", Topics in Current Chemistry, 1998, vol. 198, pp. 163-208.
Di Martino, et al., "Preparation and Physical Characterization of Forms II and III of Paracetamol", Journal of Thermal Analysis, 1997, vol. 48, pp. 447-458.
Dredge, et al., "Orally administered lenalidomide (CC-5013) is antiangiogenic in vivo and inhibits endothelial cell migration and Akt phosphorylation •in vitro", Microvascular Research, 2005, vol. 69, pp. 56-63.
Jönsson, "Chemical structure and teratogenic properties", Acta Pharmaceutica Suecica, 1972, vol. 9, pp. 521-542.
Knapman, "Polymorphic Predictions: Understanding the nature of crystalline compounds can be critical in drug development and manufacture", Modern Drug Discovery, 2000, pp. 53-57 (missing pp. 55-56 as they contain only advertisements).
Liu, et al., "Development and Validation of a Highly Sensitive Liquid Chromatography/Mass Spectrometry Method for Simultaneous Quantification of Lenalidomide and Flavopiridol in Human Plasma", Therapeutic Drug Monitoring, 2008, vol. 30(5), pp. 620-627.
Muller, et al., "Amino-Substituted Thalidomide Analogs: Potent Inhibitors of TNF-α Production", Bioorganic & Medicinal Chemistry Letters, 1999, vol. 9, pp. 1625-1630.
Murphy-Poulton, et al., "Thalidomide enantiomers: Determination in biological samples by HPLC and vancomycin-CSP", J. Chromatography B, 2006, vol. 831, pp. 48-56.
Saravanan, et al., "Development of an HPLC Assay Method for Lenalidomide", Chromatographia, 2007, vol. 66, pp. 287-290.
Sastry, et al., "New Spectrophotomeric Methods for Estimation of Lenalidomide in Pharmaceutical Formulations", International Journal of PharmTech Research, 2009, vol. 1(3), pp. 416-419.
Tohnya, et al. "Determination of CC-5013, an analogue of thalidomide, in human plasma by liquid chromatography-mass spectrometry", J. Chromatography B, 2004, vol. 811, pp. 135-141.
March, "Advanced Organic Chemistry, Reactions, Mechanisms, and Structure", Fourth Edition, 1992, pp. 918-919.
V.M. Polosin et al, Zhurnal Obshchei Khimii, 1992, vol. 62, No. 2, pp. 367-374.

* cited by examiner

PROCESS FOR THE PREPARATION OF LENALIDOMIDE

CROSS-REFERENCE TO RELATED APPLICATION(s)

This is a Section 371 National Stage Application of International No. PCT/US2010/050352, filed on 1 Mar. 2010, and published as WO 2010/100476 A1 on 10 Sep. 2010, which claims priority from IN Patent Application No. 383/KOL/2009, filed 2 Mar. 2009, and IN Patent Application No. 463/KOL/2009, filed 16 Mar. 2009, the contents of which are incorporated herein in their entirety for all purposes.

FIELD OF THE INVENTION

The present invention relates to improved processes for preparing 3-(4-amino-1-oxo-1,3-dihydro-isoindol-2-yl)-piperidine-2,6-dione (I) (lenalidomide) and its intermediate 3-(1-oxo-4-nitro-1,3-dihydro-isoindol-2-yl)-piperidine-2,6-dione. The present invention further relates to improved processes for preparing lenalidomide crystalline form A, use of said crystalline form A as an active pharmaceutical ingredient or as an intermediate in the preparation of further crystalline or amorphous forms of lenalidomide, compositions comprising lenalidomide crystalline form A and their use in the treatment of disease.

(I)

BACKGROUND OF THE INVENTION 3-(4-Amino-1-oxo-1,3-dihydro-isoindol-2-yl)-piperidine-2,6-dione (I), having the generic name lenalidomide, is a non-polypeptide compound that antagonizes TNFα and is thought to elevate levels of adenosine 3',5'-cyclic monophosphate. Lenalidomide and various structural analogues are useful in the treatment of a wide range of conditions including autoimmune disease and cancer. Structurally lenalidomide is closely related to thalidomide and is well known in the prior art (e.g. see N. Jonsson, Acta Pharm. Suecica, vol. 9, pages 521-542, 1972).

U.S. Pat. No. 5,635,517 and U.S. Pat. No. 6,281,230 describe the synthesis of lenalidomide by hydrogenating 1 g of a nitro intermediate, 3-(1-oxo-4-nitro-1,3-dihydro-isoindol-2-yl)-piperidine-2,6-dione, at 50 psi pressure for 6.5 hours using 0.13 g of 10% Pd/C catalyst in 200 ml of 1,4-dioxane.

The residue was crystallized from ethyl acetate and then from dioxane/ethyl acetate. The patents indicate the yield to be about 36%.

The same patents also describe the preparation of the nitro intermediate. 4-Nitro-phthalic anhydride is coupled with 2,6-dioxopiperidine-3-ammonium chloride in glacial acetic acid and sodium acetate to obtain 1,3-dioxo-2-(2,6-dioxopiperidin-3-yl)-5-nitro-isoindoline in 54% yield. The preparation of the nitro intermediate 3-(1-oxo-4-nitro-1,3-dihydro-isoindol-2-yl)-piperidine-2,6-dione follows the same reaction conditions as described, resulting in a low yield of the nitro intermediate of about 55%.

WO 2006/028964 describes processes for the preparation of substituted 2-(2,6-dioxopiperidin-3-yl)-1-oxo-isoindolines. The process described therein for preparing lenalidomide involves the preparation of the nitro intermediate by first coupling of an L-glutamine methyl ester with methyl 2-bromomethyl-3-nitro-benzoate in acetonitrile and cyclising the resultant N-(1-oxo-4-nitro-isoindol-2-yl)-L-glutamine methyl ester. 1 g of the nitro compound is then hydrogenated with 10% Pd/C catalyst in 600 ml of methanol at 50 psi of hydrogen for 5 hours. The solid was slurried in hot ethyl acetate and dried, resulting in a yield of 51% lenalidomide.

The prior art processes described have major disadvantages, such as:
(1) the low yield of the final product;
(2) the low yield of the nitro intermediate; and
(3) the large amount of solvent used in the hydrogenation process.

These disadvantages result in the prior art processes:
(1) being hazardous; and
(2) having poor commercial viability due to the large solvent: substrate ratio and low yield of the final product lenalidomide.

It would thus be advantageous to provide a process for the preparation of lenalidomide wherein the amount of solvent used is reduced resulting in a synthetic route that is both more economical and safer than prior art processes.

Many compounds can exist in different crystalline forms or polymorphs. These forms can exhibit varying physical, chemical and spectroscopic properties. For example, certain polymorphs of a compound may be more readily soluble in particular solvents, may flow more readily, or may compress more easily than others (e.g. see P. DiMartino et al., J. Thermal Analysis, vol. 48, pages 447-458, 1997). In the case of drugs, certain solid forms may be more bioavailable than others, while others may be more stable under certain manufacturing, storage and biological conditions. This is particularly important from a regulatory standpoint, since drugs are approved by agencies such as the U.S. Food and Drug Administration only if they meet exacting purity and characterisation standards. Indeed, the regulatory approval of one polymorph of a compound, which exhibits certain solubility and physico-chemical (including spectroscopic) properties, typically does not imply the ready approval of other polymorphs of that same compound. Polymorphic forms of a compound are known in the pharmaceutical arts to affect, for example, the solubility, stability, flowability, fractability and compressibility of the compound, as well as the safety and efficacy of drug products comprising it (e.g. see K. Knapman, Modern Drug Discovery, pages 53-57, 2000). Therefore, the discovery of new polymorphs of a drug can provide a variety of advantages.

New polymorphic forms of lenalidomide and more efficient processes for preparing them can further the development of pharmaceutical formulations and may yield numerous formulation, manufacturing and therapeutic benefits.

U.S. Pat. No. 7,465,800 describes the preparation and characterisation of a number of crystalline forms of lenalidomide, specifically forms A-H. The studies described in this patent conclude that form B is the desired polymorph for use as an active pharmaceutical ingredient (API). Form B has been used in the formulation of API into drug product for clinical studies.

The preparation of pure crystalline forms of an API provides many advantages. Pure crystalline forms of an API can be used, for example, as intermediates in preparing API for clinical studies or incorporation into final dosage forms for marketing. There is thus a need for pure crystalline forms to aid the drug formulator in his task of preparing regulatory compliant API.

SUMMARY OF THE INVENTION

The inventors have found that the careful selection of the solvents, both for the synthesis as well as the further reduction reaction of the nitro intermediate, 3-(1-oxo-4-nitro-1,3-dihydro-isoindol-2-yl)-piperidine-2,6-dione, reduces the solvent volume appreciably with a surprising improvement in the yield of the intermediate as well as the final amino compound, lenalidomide.

Thus, the present invention provides a commercially viable process for the preparation of lenalidomide resulting in a greater than 80% molar yield and, surprisingly, a chemical purity of greater than 99.9% (as measured by HPLC).

The present invention also provides a process for the preparation of the key nitro intermediate of lenalidomide, said process resulting in a greater than 90% molar yield and a chemical purity of greater than 99.8% (as measured by HPLC).

Accordingly, a first aspect of the invention provides a process for the preparation of lenalidomide, comprising the catalytic reduction of 3-(1-oxo-4-nitro-1,3-dihydro-isoindol-2-yl)-piperidine-2,6-dione, comprising:
(i) mixing the 3-(1-oxo-4-nitro-1,3-dihydro-isoindol-2-yl)-piperidine-2,6-dione in a solvent system;
(ii) contacting the resulting mixture from step (i) with a catalyst; and
(iii) contacting the mixture from step (ii) with hydrogen;
characterised in that the solvent system comprises a mixture of polar solvents.

As used herein the term "lenalidomide" includes any hydrate, solvate, polymorph or enantiomer of lenalidomide, unless otherwise specified.

As used herein the term "mixture of polar solvents" means a mixture comprising at least two polar solvents.

In one embodiment of a process according to the first aspect of the invention, the mixture of polar solvents comprises a straight or branched chain aliphatic alcohol with 1 to 5 carbon atoms and an aliphatic nitrile with 1 to 3 carbon atoms. Preferably the aliphatic nitrile is a straight chain aliphatic nitrile.

Preferably, the alcohol is selected from the group comprising methanol, ethanol or isopropanol, preferably the alcohol is methanol. In another embodiment, the nitrile is either acetonitrile or propionitrile. A particularly preferred embodiment provides a solvent system comprising acetonitrile and methanol.

In further preferred embodiments, the alcohol is present at between about 40% to 70%, more preferably at between about 45 to 55%, and most preferably the alcohol is present at about 50% of the solvent system.

In further preferred embodiments, the nitrile is present at between about 40% to 70%, more preferably at between about 45 to 55%, and most preferably the nitrile is present at about 50% of the solvent system.

In one embodiment of a process according to the first aspect of the invention, the ratio (w/v) of the nitro intermediate to the solvent system is between about 1:30 to about 1:200, preferably the ratio is between about 1:60 to about 1:100, most preferably the ratio is about 1:70. In the prior art processes, the ratio is more than 1:600.

In yet another embodiment of a process according to the first aspect of the invention, the reduction is carried out at atmospheric pressure and, in a further particularly preferred embodiment, the temperature is maintained at between about 20-40° C.

Further embodiments of the first aspect of the invention provide a process wherein the reduction is allowed to proceed for about 1-3.5 hours, most preferably the reduction is allowed to proceed for about 2.5 hours.

In another embodiment of a process according to the first aspect of the invention, the catalyst comprises palladium on charcoal, preferably the palladium on charcoal catalyst comprises a moisture content of between about 40-60%, most preferably the moisture content is about 50%.

A second aspect of the invention provides a process for the purification of lenalidomide, comprising:
(i) mixing lenalidomide in a solvent system;
(ii) preparing a lenalidomide salt; and
(iii) obtaining purified lenalidomide from the salt prepared in step (ii).

In one embodiment of a process according to the second aspect of the invention, the solvent system comprises a linear or branched chain alcohol with 1 to 5 carbon atoms and an aliphatic nitrile comprising 1 to 3 carbon atoms. Preferably the aliphatic nitrile is a straight chain aliphatic nitrile.

In one embodiment, the nitrile is either acetonitrile or propionitrile. In another embodiment, the alcohol is selected from the group comprising methanol, ethanol or isopropanol, preferably the alcohol is methanol.

In one embodiment of a process according to the second aspect of the invention, the salt is prepared by the addition of an acid in step (ii) selected from the group comprising acetic, tartaric, oxalic, malic, fumaric, hydrochloric and sulphuric acid. Preferably the acid is hydrochloric acid.

In one embodiment of a process according to the second aspect of the invention, the purified lenalidomide from step (iii) is obtained by the addition of a suitable base. Preferably the base is a secondary or tertiary aliphatic amine, preferably the base is triethylamine.

In one embodiment, the base is mixed in a suitable solvent system, which may preferably comprise a linear or branched chain aliphatic alcohol with 1 to 5 carbon atoms. In one embodiment, the alcohol is selected from the group comprising methanol, ethanol or isopropanol, preferably the alcohol is methanol.

A third aspect of the invention provides lenalidomide prepared by a process according to the first or second aspects of the invention. The lenalidomide preferably has a chemical purity of greater than about 99.5%, or greater than about 99.8%, or greater than about 99.9% (as measured by HPLC).

The third aspect of the invention further provides lenalidomide having a chemical purity of greater than about 99.5%, or greater than about 99.8%, or greater than about 99.9% (as measured by HPLC).

Preferably the lenalidomide according to the third aspect of the invention is suitable for reducing levels of TNFα and/or for elevating levels of adenosine 3',5'-cyclic monophosphate.

Preferably the lenalidomide according to the third aspect of the invention is suitable for treating an autoimmune disease, an immune disease, cancer, an oncogenic, oncological or cancerous condition, undesired angiogenesis, multiple myeloma, myelodysplastic syndromes, inflammation, an inflammatory disorder or a viral infection.

A fourth aspect of the invention provides a pharmaceutical composition comprising the lenalidomide according to the third aspect of the invention and a pharmaceutically acceptable carrier or excipient.

A fifth aspect of the invention provides use of the lenalidomide according to the third aspect of the invention in the manufacture of a medicament for treating an autoimmune disease, an immune disease, cancer, an oncogenic, oncological or cancerous condition, undesired angiogenesis, multiple myeloma, myelodysplastic syndromes, inflammation, an inflammatory disorder or a viral infection.

A sixth aspect of the invention provides a method of treating an autoimmune disease, an immune disease, cancer, an oncogenic, oncological or cancerous condition, undesired angiogenesis, multiple myeloma, myelodysplastic syndromes, inflammation, an inflammatory disorder or a viral infection, comprising administering to a patient in need thereof a therapeutically effective amount of the lenalidomide according to the third aspect of the invention.

A seventh aspect of the invention provides a process for the preparation of 3-(1-oxo-4-nitro-1,3-dihydro-isoindol-2-yl)-piperidine-2,6-dione comprising reacting 3-amino-piperidine-2,6-dione hydrochloride and methyl 2-halomethyl-3-nitro-benzoate in a solvent system, characterised in that the reaction occurs at less than about 60° C.

In one embodiment of a process according to the seventh aspect of the invention, the 3-amino-piperidine-2,6-dione hydrochloride is substantially dissolved in an organic solvent. Preferably the 3-amino-piperidine-2,6-dione hydrochloride is substantially dissolved in N,N-dimethylformamide or dimethyl sulphoxide, more preferably the 3-amino-piperidine-2,6-dione hydrochloride is substantially dissolved in N,N-dimethylformamide.

In one embodiment of a process according to the seventh aspect of the invention, the methyl 2-halomethyl-3-nitro-benzoate is methyl 2-bromomethyl-3-nitro-benzoate. In another embodiment, the methyl 2-halomethyl-3-nitro-benzoate is substantially dissolved in one or more polar solvent(s). Preferably at least one of the polar solvents is a nitrile, preferably acetonitrile.

In another embodiment of a process according to the seventh aspect of the invention, a base is added to the reaction mixture. Preferably the base is 4-dimethylaminopyridine or triethylamine.

An eighth aspect of the invention provides 3-(1-oxo-4-nitro-1,3-dihydro-isoindol-2-yl)-piperidine-2,6-dione prepared by a process according to the seventh aspect of the invention. Preferably the 3-(1-oxo-4-nitro-1,3-dihydro-isoindol-2-yl)-piperidine-2,6-dione has a chemical purity of greater than about 99.5% or greater than about 99.8% (as measured by HPLC).

The eighth aspect of the invention further provides 3-(1-oxo-4-nitro-1,3-dihydro-isoindol-2-yl)-piperidine-2,6-dione having a chemical purity of greater than about 99.5% or greater than about 99.8% (as measured by HPLC).

The inventors have further found that lenalidomide crystalline form A as disclosed in U.S. Pat. No. 7,465,800 can be prepared in pure form. Pure crystalline form A according to the present invention may be utilised as API per se or may be used as an intermediate in the preparation of any other crystalline or amorphous form, in particular crystalline form B.

The lenalidomide crystalline form A according to the present invention is anhydrous and unsolvated. It is non-hygroscopic and is currently considered to be the most thermodynamically stable anhydrous polymorph.

Figure 1:
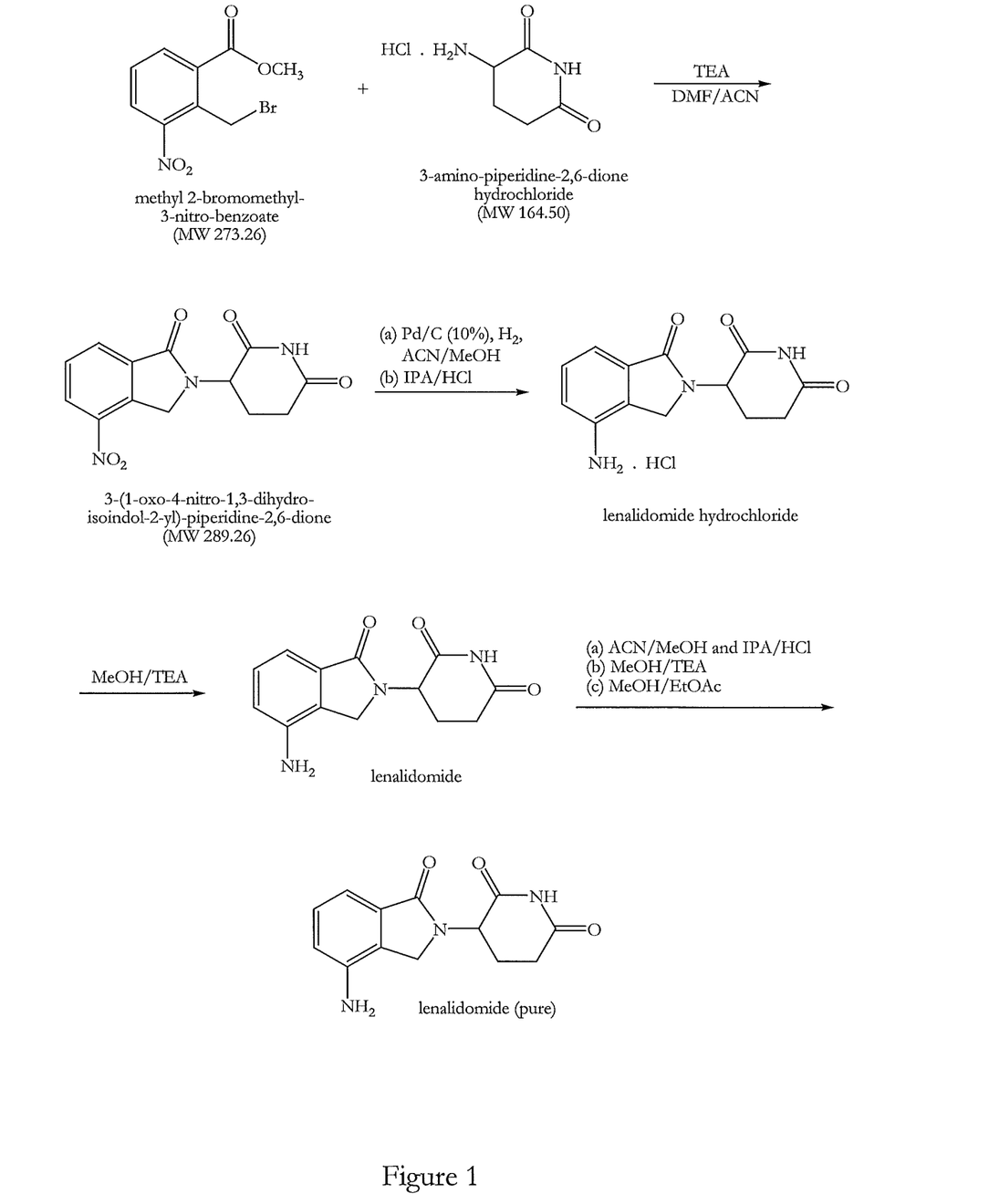
FIG. 1 shows a reaction scheme of a preferred embodiment for the preparation of lenalidomide according to the invention.
Figure 2:
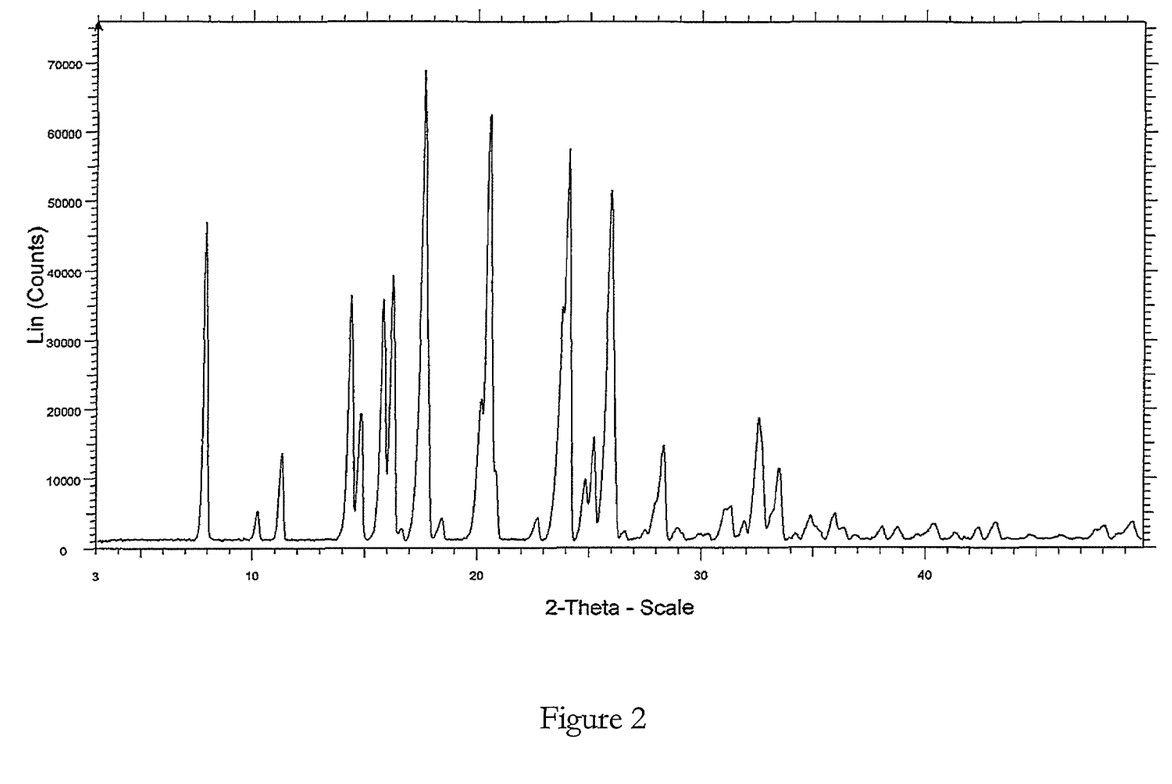
FIG. 2 is a X-Ray Powder Diffraction (XRPD) pattern of crystalline form A according to the invention.

The lenalidomide crystalline form A according to the present invention has been found to have the XRPD pattern shown in FIG. 2. Preferably the lenalidomide crystalline form A has an XRPD pattern comprising at least three peaks (preferably at least four, preferably at least five, preferably at least six, or preferably seven peaks) selected from peaks with 2θ angles of about 7.8, 14.3, 16.2, 17.6, 20.5, 24.1 and 26.0±0.2° 2θ, when copper Kα1 radiation is used.

Figure 3:
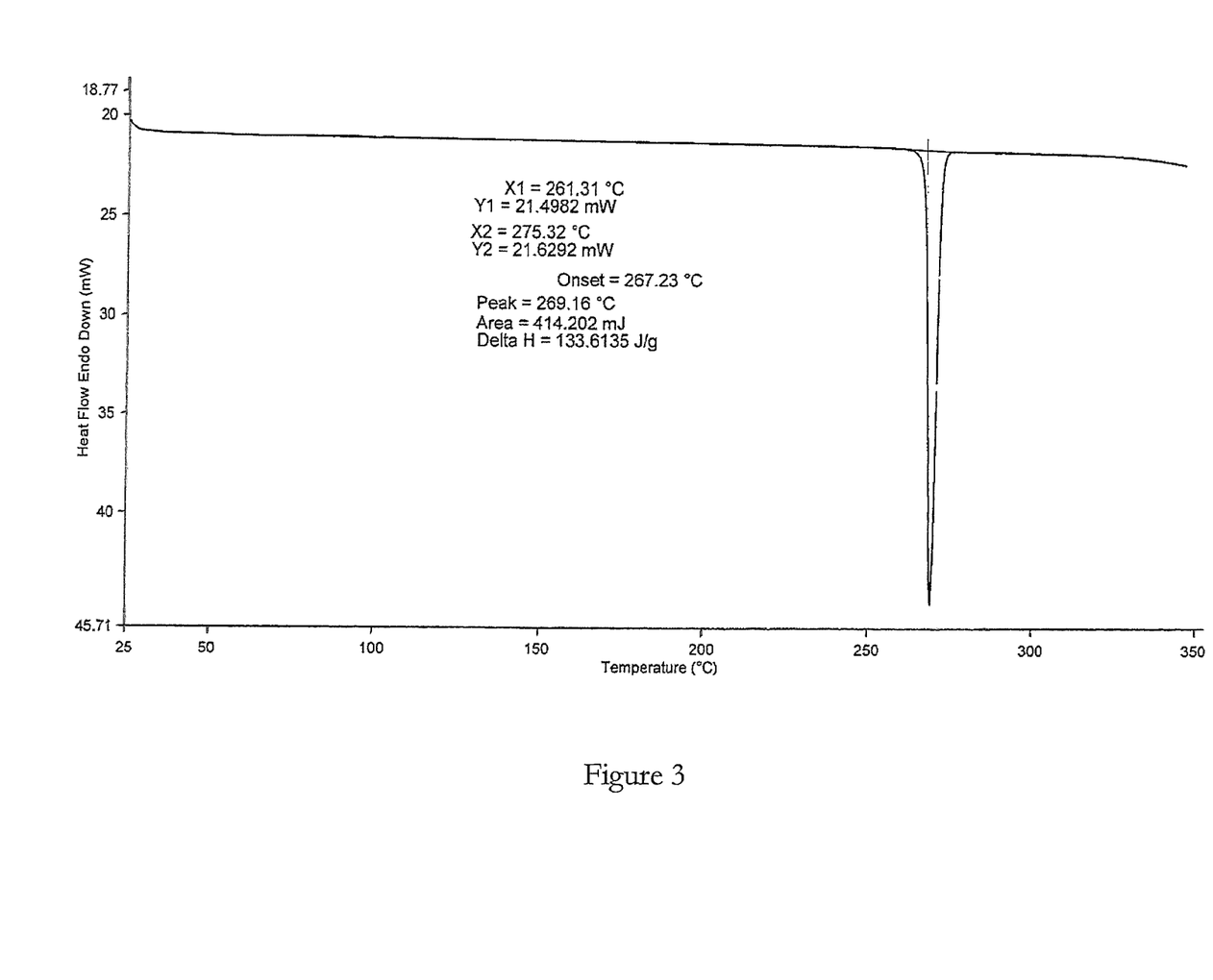
FIG. 3 is a Differential Scanning Calorimetry (DSC) thermogram of crystalline form A according to the invention.

The lenalidomide crystalline form A according to the present invention has been found to have the DSC thermogram shown in FIG. 3. Preferably the lenalidomide crystalline form A is characterised by a DSC thermogram with an endothermic peak at about 269° C.±2° C.

Figure 4:
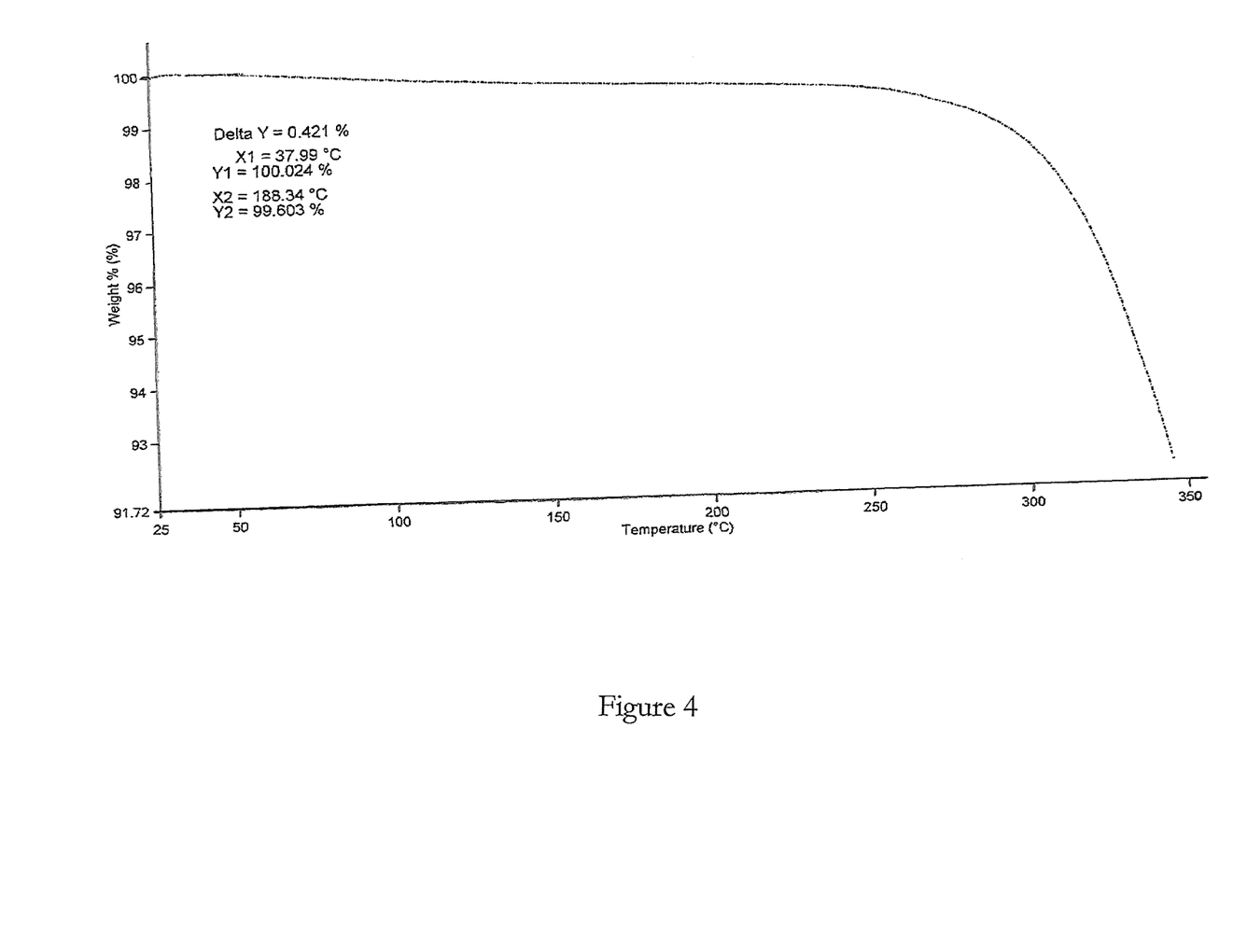
FIG. 4 is a Thermo-Gravimetric Analysis (TGA) curve of crystalline form A according to the invention.

The lenalidomide crystalline form A according to the present invention has been found to have the TGA curve shown in FIG. 4.

Accordingly, a ninth aspect of the present invention provides a process for the preparation of lenalidomide crystalline form A, comprising crystallising lenalidomide from a solvent system comprising a straight or branched chain aliphatic alcohol with 1 to 5 carbon atoms and an aliphatic ester having formula RCOOR', wherein R comprises 1 to 4 straight or branched chain carbon atoms and R' comprises 1 to 5 straight or branched chain carbon atoms.

In one embodiment, the alcohol is methanol, ethanol, n-propanol, isopropanol, or a mixture thereof, preferably the alcohol is methanol. In another embodiment, the aliphatic ester is ethyl acetate, butyl acetate, amyl acetate, or a mixture thereof, preferably the aliphatic ester is ethyl acetate. In a particularly preferred embodiment, the solvent system comprises methanol and ethyl acetate in an about 1:1 ratio v/v.

A tenth aspect of the present invention provides lenalidomide crystalline form A prepared by a process according to the ninth aspect of the present invention. Preferably the lenalidomide crystalline form A has a polymorphic purity of greater than about 90%, or greater than about 95%, or greater than about 99%, or greater than about 99.5%, or greater than about 99.9% (as measured by XRPD). Preferably the lenalidomide crystalline form A has a chemical purity of greater than about 99.5%, or greater than about 99.8%, or greater than about 99.9% (as measured by HPLC).

The tenth aspect of the present invention further provides lenalidomide crystalline form A having a polymorphic purity of greater than about 90%, or greater than about 95%, or greater than about 99%, or greater than about 99.5%, or greater than about 99.9% (as measured by XRPD). Preferably the lenalidomide crystalline form A has a chemical purity of greater than about 99.5%, or greater than about 99.8%, or greater than about 99.9% (as measured by HPLC).

Preferably the lenalidomide crystalline form A according to the tenth aspect of the present invention is suitable for use as an intermediate in the preparation of crystalline lenalidomide. Preferably the crystalline lenalidomide prepared has a polymorphic purity of greater than about 90%, or greater than about 95%, or greater than about 99%, or greater than about 99.5%, or greater than about 99.9% (as measured by XRPD). Preferably the crystalline lenalidomide prepared has a chemical purity of greater than about 99.5%, or greater than about 99.8%, or greater than about 99.9% (as measured by HPLC).

Preferably the lenalidomide crystalline form A according to the tenth aspect of the present invention is suitable for use as an intermediate in the preparation of lenalidomide crystalline form B. Preferably the lenalidomide crystalline form B has a polymorphic purity of greater than about 90%, or greater than about 95%, or greater than about 99%, or greater than about 99.5%, or greater than about 99.9% (as measured by XRPD). Preferably the lenalidomide crystalline form B has a chemical purity of greater than about 99.5%, or greater than about 99.8%, or greater than about 99.9% (as measured by HPLC).

Preferably the lenalidomide crystalline form A according to the tenth aspect of the present invention is suitable for reducing levels of TNFα and/or for elevating levels of adenosine 3',5'-cyclic monophosphate.

Preferably the lenalidomide crystalline form A according to the tenth aspect of the present invention is suitable for treating an autoimmune disease, an immune disease, cancer, an oncogenic, oncological or cancerous condition, undesired angiogenesis, multiple myeloma, myelodysplastic syndromes, inflammation, an inflammatory disorder or a viral infection.

An eleventh aspect of the present invention provides a pharmaceutical composition comprising lenalidomide crystalline form A according to the tenth aspect of the present invention and one or more pharmaceutically acceptable excipients.

A twelfth aspect of the present invention provides use of lenalidomide crystalline form A according to the tenth aspect of the present invention in the manufacture of a medicament for treating an autoimmune disease, an immune disease, cancer, an oncogenic, oncological or cancerous condition, undesired angiogenesis, multiple myeloma, myelodysplastic syndromes, inflammation, an inflammatory disorder or a viral infection.

A thirteenth aspect of the present invention provides a method of treating an autoimmune disease, an immune disease, cancer, an oncogenic, oncological or cancerous condition, undesired angiogenesis, multiple myeloma, myelodysplastic syndromes, inflammation, an inflammatory disorder or a viral infection, comprising administering to a patient in need thereof a therapeutically effective amount of lenalidomide crystalline form A according to the tenth aspect of the present invention.

A fourteenth aspect of the present invention provides a kit comprising lenalidomide crystalline form A according to the tenth aspect of the present invention or a composition according to the eleventh aspect of the present invention, and further comprising a means for substantially preventing the ingress of moisture. In one embodiment, the means is selected from a desiccant or a moisture impermeable barrier or a combination thereof.

DETAILED DESCRIPTION OF THE INVENTION

The inventors have found that lenalidomide according to the first aspect of the invention can be prepared from its nitro intermediate, 3-(1-oxo-4-nitro-1,3-dihydro-isoindol-2-yl)-piperidine-2,6-dione, in higher yield and purity by catalytic reduction. The reaction according to the invention utilises a surprisingly reduced amount of solvent as compared to the prior art. Another advantage of the invention over the prior art is that the reduction reaction proceeds at atmospheric pressure. This is contrary to the teaching in the prior art processes where similar reactions are carried out at about 50 psi, approximately 3.5 atmospheres.

A first aspect of the invention provides a process for the preparation of lenalidomide, comprising the catalytic reduction of 3-(1-oxo-4-nitro-1,3-dihydro-isoindol-2-yl)-piperidine-2,6-dione, comprising:
(i) mixing the 3-(1-oxo-4-nitro-1,3-dihydro-isoindol-2-yl)-piperidine-2,6-dione in a solvent system;
(ii) contacting the resulting mixture from step (i) with a catalyst; and
(iii) contacting the mixture from step (ii) with hydrogen;
characterised in that the solvent system comprises a mixture of polar solvents.

In particularly preferred embodiments, the 3-(1-oxo-4-nitro-1,3-dihydro-isoindol-2-yl)-piperidine-2,6-dione, herein referred to as the "nitro intermediate", is mixed in a solvent system comprising two or more polar solvents. In one embodiment of the first aspect of the invention, the mixture of polar solvents comprises a straight or branched chain aliphatic alcohol with 1 to 5 carbon atoms and an aliphatic nitrile with 1 to 3 carbon atoms. Preferably the aliphatic nitrile is a straight chain aliphatic nitrile.

Preferably, the alcohol is selected from the group comprising methanol, ethanol or isopropanol and, in another embodiment, the nitrile is either acetonitrile or alternatively propionitrile. The inventors have found that a mixture of polar solvents can solubilise the product lenalidomide to a greater extent than has been described previously. In particular, a solvent system comprising acetonitrile and methanol has been found to be especially advantageous resulting in the reduction of solvent utilised by a factor of up to 10.

In further preferred embodiments, the alcohol is present at between about 20% to 80%, more preferably at between about 45 to 55%, and most preferably the alcohol is present at about 50%. A particularly preferred embodiment provides a solvent system comprising a 1:1 v/v mixture of acetonitrile and methanol.

In a further embodiment of a process according to the first aspect, the ratio (w/v) of the nitro intermediate to the solvent system is between about 1:30 to about 1:200, preferably the ratio is between about 1:60 to about 1:100, most preferably the ratio is about 1:70. The inventors have found that at this ratio there is an excellent balance between minimum solvent used and the efficacy of the synthetic process.

In yet another embodiment according to the first aspect, the reduction is carried out at atmospheric pressure. This provides several advantages over the prior art processes. Firstly, special apparatus to maintain the reaction at the increased pressures of the prior art are not needed, making the process of the invention more economical and energy efficient.

Secondly, reaction at atmospheric pressure is less dangerous than at the increased pressures of the prior art, meaning the process of the invention is safer. Finally, the reaction at atmospheric pressure is more amenable to scale up for commercial quantities.

In preferred embodiments according to the first aspect, the reduction process can comprise bubbling hydrogen gas into the reaction mixture. The inventors have found that performing the reduction process according to the invention at temperatures between about 20-40° C. results in a greatly improved impurity profile.

The purity of an active pharmaceutical ingredient (API) is a very important consideration when developing a pharmaceutical product to be marketed. It is advantageous when a relatively pure product can be obtained from the synthetic process with as few subsequent purification steps as possible. The purification steps can add to the cost of the process and reduce the overall yield of the API thereby further adding to the cost. The inventors have found that when the reaction according to the invention was performed at below about 20° C. and above about 40° C., the reaction time increased and unknown impurities were formed. Thus maintaining the reaction within these parameters is preferable to prepare lenalidomide economically and with increased purity. In particular, maintaining the temperature at between about 32-35° C. provided the best results.

The prior art processes require a reaction time of a minimum of 5 hours. Contrastingly, in certain embodiments of a process according to the first aspect of the invention, the reduction is allowed to proceed for about 1-3.5 hours, and in a particularly preferred embodiment for about 2.5 hours. The inventors have found that there is a direct correlation between increased reaction time and the formation of impurities. Experiments by the inventors have shown that reaction times exceeding more than about 3.5 hours resulted in the formation of impurities and reduced the yield of lenalidomide. Thus the process according to the invention is able to produce lenalidomide with at least an ICH compliant purity profile without the need for costly and time-consuming purification steps.

In another embodiment of a process according to the first aspect of the invention, the catalyst comprises palladium on carbon and is added to the reaction mixture. In a particularly preferred embodiment, the palladium comprises 10% of the catalyst. The skilled person will be aware that the catalyst palladium (10%) on carbon should preferably be charged in an inert atmosphere preferably with nitrogen. The inert atmosphere before the addition of the palladium catalyst can also be generated by other noble gases such as helium. Charging in an inert atmosphere is required as such metal catalysts are pyrophoric in nature. Most preferably, the palladium on carbon catalyst, herein referred to as Pd/C, comprises a moisture content of between about 40-60%, most preferably the moisture content is about 50%. There is no mention in the prior art of the use of a Pd/C catalyst having a moisture content of between about 40-60%, most preferably a moisture content of about 50%. The inventors have found that a catalyst having said moisture content according to the invention moderates the activity of the catalyst and prevents the formation if impurities. Experiments by the inventors have shown that where the Pd/C catalyst has a moisture content of less than about 40-60%, the quality of the resultant lenalidomide was found to be inferior due to the formation of certain impurities. Preferably, the quantity of the catalyst added is between about 5-20% with respect to the nitro intermediate substrate. Most preferably, the quantity is between about 5-15%. In certain embodiments the catalyst can be added all at once or in alternative embodiments the catalyst can be divided, preferably into equal quantities, and added to the reaction mixture at varying or equally divided intervals. It was found that addition of the catalyst in multiple lots gave a better quality of product in that the formation of unknown impurities formed during the reaction was better controlled.

Preferably on completion of the reaction the resultant lenalidomide is dissolved completely in the solvent system and only catalyst is left suspended in the reaction mixture. This of course means that it is very easy to separate the lenalidomide in solution from the catalyst and any undissolved impurities. Preferably the catalyst is removed by filtration.

After completion of the reduction reaction the lenalidomide product can be easily isolated as such or isolated as an addition salt by any means available to the skilled person. The inventors have found that isolation as a salt is particularly advantageous. Firstly, if the salt is less soluble than the base in a given solvent it is easier to separate by physical means. Secondly, isolation utilising a salt form of lenalidomide has the added benefit of resulting in lenalidomide of increased purity. In this regard the inventors have found that preparation of the hydrochloride salt and subsequent liberation of the lenalidomide by the addition of a base results in a particularly pure product. Salts of lenalidomide can be prepared in conventional fashion known to the skilled person by addition of the corresponding acid to the reaction mixture. Examples of acids that can be used comprise organic acids such as those resulting in the acetate, tartrate, oxalate, malate and fumarate salts, and inorganic acids such as hydrochloric acid and sulphuric acid. In a particularly preferred embodiment gaseous hydrochloric acid is dissolved in an organic solvent which in further embodiments may comprise one or more straight or branched chain $C_1$ to $C_5$ alcohols. In preferred embodiments the alcohol is methanol or alternatively isopropanol. In a particularly preferred embodiment the hydrochloric acid solution is prepared by dissolving hydrogen chloride gas in isopropanol. In those embodiments wherein a salt of lenalidomide is prepared, the purified lenalidomide base can be liberated by hydrolysis with a suitable organic base, for example, secondary or tertiary alkyl amines. In preferred embodiments, triethylamine can be added to liberate lenalidomide as a free base.

The skilled person will of course realise that purification, which in preferred embodiments is the acid-base purification described above, can be performed either as part of the isolation process or as an additional step wherein the isolated lenalidomide is resuspended in an appropriate solvent or a mixture of solvents. Accordingly there is provided in a second aspect according to the invention a process for the purification of lenalidomide comprising:
(i) mixing lenalidomide in a solvent system;
(ii) forming a lenalidomide salt; and
(iii) obtaining pure lenalidomide from the salt prepared in step (ii).

It is envisaged that the lenalidomide in step (i) may comprise any form of lenalidomide, for example, lenalidomide base or a salt thereof.

The skilled person will of course realise that the embodiments described previously relating to purification are also relevant to the second aspect of the invention.

Accordingly, a particularly preferred purification process comprises acid-base purification wherein a lenalidomide salt is prepared by reaction of lenalidomide salt or base with an inorganic or organic acid. A particularly preferable acid is a methanol or alternatively an isopropanol solution of gaseous hydrochloric acid. After addition of the acid to the lenalidomide base or salt and after isolation of the lenalidomide salt, the pure lenalidomide is liberated by the addition of an appropriate base. Most preferably the base is selected from a secondary or tertiary alkyl amine, most preferably triethylamine. The inventors have found that lenalidomide purified via a hydrochloride salt as described results in a product having a particularly high chemical purity of greater than 99.9% as measured by HPLC.

The processes according to the first and second aspects of the invention result in lenalidomide having a chemical purity not described in the prior art. The inventors have found that lenalidomide purified via a suitable salt results in a product having further increased purity. In a particularly preferred embodiment, lenalidomide purified by liberation from the hydrochloride salt was found to have a particularly high chemical purity of the order of greater than 99.9% as measured by HPLC.

Accordingly a third aspect of the invention provides lenalidomide having a chemical purity of greater than 99.5%, most preferably having a chemical purity of greater than 99.8%, and in a most preferred embodiment greater than 99.9% (as measured by HPLC).

The lenalidomide obtained is preferably dried by any means known to the skilled person. The drying temperature is selected to provide a balance between speed and preventing thermal degradation of the product. Such conditions are within the skill set of the skilled person to identify. The inventors have found that preferably the drying temperature is kept at between about 45-50° C. at 100 mmHg pressure for approximately 3 hours.

A seventh aspect of the invention provides a process for the preparation of 3-(1-oxo-4-nitro-1,3-dihydro-isoindol-2-yl)-piperidine-2,6-dione comprising reacting 3-amino-piperidine-2,6-dione hydrochloride and methyl 2-halomethyl-3-nitro-benzoate in a solvent system, characterised in that the reaction occurs at less than about 60° C. The prior art processes involve vigorous reaction conditions such as higher reaction temperatures required for maintaining reflux in high boiling solvents such as N,N-dimethylformamide.

In one embodiment, the 3-amino-piperidine-2,6-dione hydrochloride is substantially dissolved in an organic solvent, preferably the solvent is N,N-dimethylformamide or dimethyl sulphoxide, more preferably the solvent is N,N-dimethylformamide.

In another embodiment according to the seventh aspect of the invention, the methyl 2-halomethyl-3-nitro-benzoate is methyl 2-bromomethyl-3-nitro-benzoate. In particularly preferred embodiments, the methyl 2-halomethyl-3-nitro-benzoate is substantially dissolved in one or more polar solvent(s). In a preferred embodiment at least one of the polar solvents is a nitrile. Most preferably the nitrile is acetonitrile.

Another embodiment according to the seventh aspect of the invention provides a process wherein a base is added to the reaction mixture, preferably the base is selected from 4-dimethylaminopyridine and triethylamine.

The process according to the invention for preparing 3-(1-oxo-4-nitro-1,3-dihydro-isoindol-2-yl)-piperidine-2,6-dione results in said compound having a chemical purity not described in the prior art. Accordingly an eighth aspect provides 3-(1-oxo-4-nitro-1,3-dihydro-isoindol-2-yl)-piperidine-2,6-dione having a chemical purity of greater than 99.5%, most preferably having a chemical purity of greater than 99.8% (as measured by HPLC).

Particularly preferred embodiments of the seventh aspect of the invention provide the preparation of the nitro intermediate, 3-(1-oxo-4-nitro-1,3-dihydro-isoindol-2-yl)-piperidine-2,6-dione), comprising the following steps:
(a) mixing 3-amino-piperidine-2,6-dione hydrochloride in N,N-dimethylformamide;
(b) adding an organic base, preferably 4-dimethylaminopyridine or alternatively triethylamine;
(c) adding methyl 2-halomethyl-3-nitro-benzoate in a polar solvent, preferably a nitrile, most preferably acetonitrile, whilst stirring;
(d) heating the reaction mixture from step (c) to a temperature of less than 60° C. until completion of the reaction, most preferably for about 5 to 10 hours;
(e) removing around two thirds of the solvent, preferably by distillation under reduced pressure, and in further embodiments at less that 60° C.

Further steps to isolate and further purify the nitro intermediate, if needed, may comprise:
(a) washing the residual quantity of reaction mixture with hot water, then isolating the 3-(1-oxo-4-nitro-1,3-dihydro-isoindol-2-yl)-piperidine-2,6-dione, preferably by cooling and then filtration;
(b) washing the isolated solid again with warm water and then with methanol to remove impurities.

In particularly preferred embodiments, the isolated solid is dried, preferably at between about 50-60° C., preferably at between about 50-55° C., preferably under reduced pressure, to obtain a purple to ash coloured solid.

As used herein the term "mixture" may include fully or partially dissolved solutes in solutions, suspensions and colloids etc.

U.S. Pat. No. 7,465,800 is silent as to the polymorphic purity of any of the forms disclosed therein apart from forms B and E. Form A is disclosed as being obtained by crystallisation from various solvents including 1-butanol, butyl acetate, ethanol, ethyl acetate, methanol, methyl ethyl ketone and tetrahydrofuran. However it is beyond the skilled person's non-inventive capabilities to determine, without undue burden, which solvent system would result in the preparation of pure crystalline form A. Indeed there is no teaching or even motivation that would lead the skilled person to even suggest which would be the best solvent or combination of solvents providing a pure crystalline form A.

The inventors have found that crystallising lenalidomide from a previously undisclosed mixture of specific solvents, results in a pure crystalline form suitable for use as an API per se or suitable for use as an intermediate in the preparation of other crystalline or amorphous forms of lenalidomide.

Accordingly in a ninth aspect according to the invention there is provided a process for the preparation of lenalidomide crystalline form A, comprising crystallising lenalidomide from a solvent system comprising a straight or branched chain aliphatic alcohol with 1 to 5 carbon atoms and an aliphatic ester having formula RCOOR', wherein R comprises 1 to 4 straight or branched chain carbon atoms and R' (alcohol portion) comprises 1 to 5 straight or branched chain carbon atoms. It will be apparent to the skilled person that any form of crude lenalidomide may be utilised. Mixtures of different crystalline forms of lenalidomide may also be crystallised into the desired crystalline form A according to the invention.

It has been found that crystallising lenalidomide from such a mixture of solvents results in a product with greater than 90%, preferably greater than 95% polymorphic purity (as measured by XRPD).

In preferred embodiments of the ninth aspect the alcohol is methanol and in further preferred embodiments the ester is ethyl acetate. In a particularly preferred embodiment the mixture of solvents comprises ethyl acetate and methanol, which most preferably are in a ratio of 1:1 v/v. This particular ratio of methanol and ethyl acetate has been shown to result in a product with a chemical purity of greater than 99%, preferably greater than 99.5% and most preferably greater than 99.9% as determined by HPLC, area normalisation method.

In a tenth aspect according to the invention, lenalidomide crystalline form A is prepared according to any of the embodiments of the ninth aspect, for use as an intermediate in the preparation of pure crystalline lenalidomide. Of course it will be understood that the final lenalidomide crystalline form will be dependent on the conditions of crystallisation. The conditions for preparing polymorphs B—H of lenalidomide are given in U.S. Pat. No. 7,465,800. For example, form B can be crystallised from hexane, toluene and water, and form C can be obtained from evaporations, slurries and slow cools in acetone solvent systems. The disclosure relating to the preparation and characterisation of forms A-H from U.S. Pat. No. 7,465,800 is hereby incorporated by reference in its entirety. In particular the inventors have determined that form A is the most thermodynamically stable form. In fact form B will convert to form A under conditions of heating.

Once the pure form A has been obtained it may be isolated by any means common in the field or known to the skilled artisan. In one embodiment the solid is obtained by filtration of the solvent. Preferably the filtered solid is obtained by vacuum filtration. Preferably the product is dried at a temperature that does not induce conversion of the crystalline form A or cause it to degrade. The inventors have found that drying the product at between about 50-55° C. at a pressure of between about 150-200 mmHg until a constant weight is obtained is particularly preferable.

In an eleventh aspect of the invention a pharmaceutical composition is provided, comprising lenalidomide prepared according to the ninth aspect of the invention or comprising lenalidomide according to the tenth aspect of the invention, and one or more pharmaceutically acceptable excipients.

Further form A has been found to convert to form B in aqueous solvent systems. This may be undesirable in some embodiments of the invention. Accordingly in a fourteenth aspect a kit is provided comprising a composition according to the eleventh aspect and further comprising a means for substantially preventing the ingress of moisture. Preferably the means is selected from a desiccant or compound able to reduce or remove moisture from the immediate atmosphere of the composition. Another preferred means is a moisture impermeable barrier. Any examples known to the skilled person that achieve the aim of preventing moisture reaching the composition may be employed, for example, silica as a desiccant or blister packs comprising the compositions according to the invention. The means for preventing moisture ingress may also be employed in combination. The most suitable means for preventing said moisture ingress is well with the skill set of the skilled person to determine.

Lenalidomide prepared according to the invention may be administered per se or more preferably in a pharmaceutical composition. Accordingly, the present invention also provides a pharmaceutical composition comprising lenalidomide prepared according to the invention or crystalline forms of lenalidomide according to the invention, and further comprising one or more pharmaceutically acceptable excipients.

As used herein the term "pharmaceutically acceptable" embraces compounds, compositions and ingredients for both human and veterinary use.

Oral dosage forms include tablets, capsules, dragees, and similar shaped, compressed pharmaceutical forms containing from 1 to 100 mg of drug per unit dosage. Isotonic saline solutions containing from 5 to 100 mg/ml can be used for parenteral administration which includes intramuscular, intrathecal, intravenous and intra-arterial routes of administration. Rectal administration can be effected through the use of suppositories formulated from conventional carriers such as cocoa butter.

The composition may, if desired, be in the form of a pack accompanied by written or printed instructions for use.

Usually the pharmaceutical compositions of the present invention will be adapted for oral administration. Particularly suitable compositions for oral administration are unit dosage forms such as tablets and capsules, in particular capsules. Other fixed unit dosage forms, such as powders presented in sachets, may also be used.

In preparing such compositions the active pharmaceutical ingredient, in this case lenalidomide, is usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum, acacia, calcium silicate, microcrystalline cellulose, polyvinylpyrrolidinone, cellulose, water, syrup, and methyl cellulose. The formulations can additionally include lubricating agents such as talc, magnesium stearate and mineral oil, wetting agents, emulsifying and suspending agents, preserving agents such as methyl- and propyl-hydroxybenzoates, sweetening agents or flavouring agents.

The details of the invention, its objects and advantages are explained hereunder in greater detail in relation to non-limiting exemplary illustrations.

EXAMPLES

Example 1

Preparation of 3-(1-oxo-4-nitro-1,3-dihydro-isoindol-2-yl)-piperidine-2,6-dione

Triethylamine (140.8 g, 2.29 mol) was added at 25-30° C. to a solution of 3-amino-piperidine-2,6-dione hydrochloride (100 g, 0.61 mol) in N,N-dimethylformamide (800 ml). A solution of methyl 2-bromomethyl-3-nitro-benzoate (186.0 g, 1.13 mol) in acetonitrile (200 ml) was then added under stirring and a nitrogen atmosphere and the reaction mixture was heated to 50-55° C. for 8-10 hours. After completion of the reaction approximately 60% solvent was removed by distillation at 50-60° C. under reduced pressure (100 mbar). Water (1000 ml) was added to the residual mixture at 50-55° C. and stirred for 1 hour at this temperature. The resultant solid product was cooled to 25-30° C. and filtered. The solid was washed with water (500 ml) at 50-55° C., cooled at ambient temperature and filtered again. Finally the solid was washed with methanol (500 ml) at 50-55° C., cooled at 25-30° C. and filtered. The filtered solid product was dried at 50-55° C. under low pressure (200 mmHg) for 4 hours to give 3-(1-oxo-4-nitro-1,3-dihydro-isoindol-2-yl)-piperidine-2,6-dione as a purple to ash coloured solid.

Yield: 145-155 g (83-88%)

HPLC purity: 99.8% (by area normalisation)

Example 2

Preparation of 3-(4-amino-1-oxo-1,3-dihydro-isoindol-2-yl)-piperidine-2,6-dione (I) (lenalidomide)

3-(1-Oxo-4-nitro-1,3-dihydro-isoindol-2-yl)-piperidine-2,6-dione (100 g, 0.35 mol) was dissolved in an acetonitrile and methanol mixture (7000 ml, 1:1, v/v). A catalyst comprising a slurry of 10% Pd on charcoal (5.0 g) in methanol (25 ml) and having a moisture content of about 50% was added under a nitrogen atmosphere. The nitrogen gas was replaced with hydrogen gas and bubbled through the reaction mixture whilst stirring. The reaction mixture was maintained at 30-35° C. After one hour a second amount of the catalyst was added and the hydrogen bubbling continued until completion of the reaction after a total time of approximately 2-2.5 hours. Completion of the reaction was monitored by TLC. The catalyst was completely removed by filtration. The filtrate was concentrated by distillation at 45-50° C. temperature and 80-100 mmHg pressure and approximately two thirds of the solvent were removed. An equimolar amount of hydrogen chloride as an isopropanol solution was slowly added to the residual slurry. The mixture was then cooled to between about 5-10° C. and the resulting solid hydrochloride salt of lenalidomide was filtered, washed with methanol and dried.

The filtered lenalidomide hydrochloride was resuspended in methanol (500 ml) and triethylamine (1.1 mole equivalent) was slowly added to the reaction mixture. The reaction mixture was cooled to 5-10° C. and the liberated lenalidomide was filtered, washed with methanol and dried.

Yield: 70 g (78%)
HPLC purity: ~99.5% (by area normalisation)

Example 3

Further Purification of Lenalidomide

Lenalidomide was prepared as above.

Lenalidomide (70 g) was suspended in a mixture of acetonitrile and methanol (700 ml, 1:1, v/v) and a solution of hydrogen chloride in isopropanol in equimolar portion of crude lenalidomide was slowly added. The reaction mixture was stirred for 45 minutes at ambient temperature and then slowly cooled to 5-10° C. and maintained at this temperature for a further 45 minutes. The precipitated solid was filtered and dried. The solid was washed in methanol (100 ml) at ambient temperature and filtered and dried to remove all the solvent.

The lenalidomide hydrochloride salt was suspended in methanol (350 ml) and 1.1 mole equivalent of triethylamine was slowly added whilst stirring. The reaction mixture was stirred at ambient temperature for the next 45 minutes and then cooled at 5-10° C. and maintained at the same temperature for the next 45 minutes. The precipitated solid was filtered and dried. It was then washed with methanol (105 ml) and the resultant lenalidomide isolated by filtration. The pure product was dried at 50-55° C. and 150-200 mmHg pressure for about 7-8 hours.

Yield: 65 g (93%)
HPLC purity: ~99.9% (by area normalisation)

Example 4

Preparation of Crystalline Form A

Lenalidomide (70 g) as prepared in example 2 or 3 was stirred with a mixture of ethyl acetate and methanol (700 ml, 1:1, v/v) for 1-1.5 hours and isolated by vacuum filtration. The product was then dried at 50-55° C. and at 150-200 mmHg pressure for 7-8 hours to obtain pure lenalidomide crystalline form A, which was characterised by the XRPD pattern, DSC thermogram and TGA curve shown in FIGS. 2-4 respectively.

Yield: 65 g (93%)
HPLC purity: ~99.9% (area normalisation method)
Polymorphic purity: ~99.9% (measured by XRPD)

The XRPD analysis was performed on a Bruker D8 Advance diffractometer, using a copper K$\alpha$1 radiation source. The DSC analysis was performed on a Perkin Elmer Pyris 6 spectrophotometer and recorded over a temperature range of 25-350° C. at a heating rate of 10° C./min. The TGA analysis was performed on a Perkin Elmer Pyris 1 spectrophotometer and recorded over a temperature range of 25-350° C. at a heating rate of 10° C./min.

It will be understood that the present invention has been described above by way of example only. The examples are not intended to limit the scope of the invention. Various modifications and embodiments can be made without departing from the scope and spirit of the invention, which is defined by the following claims only.

What is claimed is:

1. A process for the preparation of lenalidomide, comprising the catalytic reduction of 3-(1-oxo-4-nitro-1,3-dihydro-isoindol-2-yl)-piperidine-2,6-dione, comprising:
   (i) mixing the 3-(1-oxo-4-nitro-1,3-dihydro-isoindol-2-yl)-piperidine-2,6-dione in a solvent system;
   (ii) contacting the resulting mixture from step (i) with a catalyst; and
   (iii) contacting the mixture from step (ii) with hydrogen;
   characterised in that the solvent system comprises a mixture of polar solvents, wherein the mixture of polar solvents comprises a straight or branched chain aliphatic alcohol with 1 to 5 carbon atoms and an aliphatic nitrile with 1 to 3 carbon atoms, wherein the aliphatic nitrile is present at between 40% to 70% of the solvent system.

2. A process according to claim 1, wherein:
   (a) the alcohol is methanol, ethanol or isopropanol; and/or
   (b) the aliphatic nitrile is acetonitrile or propionitrile; and/or
   (c) the solvent system comprises acetonitrile and methanol; and/or
   (d) the alcohol is present at between 40% to 60% of the solvent system.

3. A process according to claim 1, wherein:
   (a) the ratio of the 3-(1-oxo-4-nitro-1,3-dihydro-isoindol-2-yl)-piperidine-2,6-dione to the solvent system is between 1:30 to 1:200; and/or
   (b) the reduction is carried out at atmospheric pressure; and/or
   (c) the reduction is maintained at between 20-40° C.; and/or
   (d) the reduction is allowed to proceed for 1-3.5 hours; and/or
   (e) the catalyst comprises palladium on charcoal.

4. A process according to claim 1, further comprising the purification of lenalidomide, comprising:
   (i) mixing lenalidomide in a solvent system;
   (ii) preparing a lenalidomide salt; and
   (iii) obtaining purified lenalidomide from the salt prepared in step (ii).

5. A process according to claim 4, wherein the solvent system comprises a straight or branched chain alcohol with 1 to 5 carbon atoms and an aliphatic nitrile comprising 1 to 3 carbon atoms.

6. A process according to claim 5, wherein:
   (a) the aliphatic nitrile is acetonitrile or propionitrile; and/or
   (b) the alcohol is methanol, ethanol or isopropanol; and/or
   (c) the alcohol is methanol.

7. A process according to claim 4, wherein:
   (a) the salt is prepared by the addition of an acid in step (ii) selected from the group comprising acetic, tartaric, oxalic, malic, fumaric, hydrochloric and sulphuric acid; and/or
   (b) the salt is prepared by the addition of hydrochloric acid in step (ii).

8. A process according to claim 4, wherein the purified lenalidomide from step (iii) is obtained by the addition of a base.

9. A process according to claim 8, wherein:
   (a) the base is a secondary or tertiary aliphatic amine; and/or
   (b) the base is triethylamine; and/or
   (c) the base is mixed in a solvent system; and/or
   (d) the base is mixed in a solvent system, wherein the solvent system comprises a straight or branched chain aliphatic alcohol with 1 to 5 carbon atoms; and/or (e) the base is mixed in a solvent system, wherein the solvent system comprises methanol, ethanol or isopropanol; and/or (f) the base is mixed in a solvent system, wherein the solvent system comprises methanol.

* * * * *